United States Patent [19]

Narayan

[11] Patent Number: 4,738,991
[45] Date of Patent: Apr. 19, 1988

[54] STORAGE STABLE POLYISOCYANATES CHARACTERIZED BY ALLOPHANATE LINKAGES

[75] Inventor: Thirumurti Narayan, Grosse Ile, Mich.

[73] Assignee: BASF Corporation, Wyandotte, Mich.

[21] Appl. No.: 6,072

[22] Filed: Jan. 23, 1987

[51] Int. Cl.$^4$ ............................................. C08C 18/30
[52] U.S. Cl. ..................................... 521/124; 521/155; 521/157; 521/170; 521/172; 521/174; 528/48; 528/49; 528/55; 528/56; 528/76; 528/80; 528/85
[58] Field of Search ............... 521/124, 155, 157, 170, 521/172, 174; 528/48, 49, 55, 56, 76, 80, 85

[56] References Cited

U.S. PATENT DOCUMENTS

| | | | |
|---|---|---|---|
| 3,769,318 | 10/1973 | Windemuth et al. | 521/124 |
| 4,160,080 | 7/1979 | Köenig et al. | 528/59 |
| 4,177,342 | 12/1979 | Bock et al. | 528/49 |

FOREIGN PATENT DOCUMENTS 994890  6/1965  United Kingdom .

Primary Examiner—Maurice J. Welsh
Assistant Examiner—S. A. Acquah
Attorney, Agent, or Firm—Norbert M. Lisicki

[57] ABSTRACT

Organic polyisocyanates characterized by allophanate linkages are prepared by reacting an organic polyisocyanate with a mono- or polyhydric compound in the presence of an organo metal catalyst. The catalyst is then deactivated using a compound such as an inorganic acid, organic acid, organic chloroformate or an organic acid chloride. The isocyanates are useful in preparing polyurethane foams.

6 Claims, No Drawings

STORAGE STABLE POLYISOCYANATES CHARACTERIZED BY ALLOPHANATE LINKAGES

BACKGROUND OF THE INVENTION

1. Field of the Invention

The present invention concerns storage stable organic polyisocyanates. More particularly, the present invention relates to storage stable polyisocyanates characterized by allophanate linkages.

2. Prior Art

U.S. Pat. No. 3,769,318 teaches the preparation of allophanate containing polyisocyanates by reacting N-substituted carbonic acid esters with organic polyisocyanates in the presence of a compound having an alkylating effect. These alkylating compounds prevent trimerization side reactions. British patent No. 994,890 teaches the preparation of allophanate polyisocyanates employing metal or amine catalysts.

SUMMARY OF THE INVENTION

Storage stable organic polyisocyanates characterized by allophanate linkages are prepared by reacting an excess of an organic polyisocyanate with a mono or polyhydroxy compound in the presence of an organo metal catalyst. After the allophanate reaction has proceeded to the desired extent the reaction is terminated by deactivating the catalyst by an inorganic acid, organic acid or an organic acid chloride. These compounds also prevent the degradation of the allophanate containing isocyanate compositions of the present invention during long term storage.

DESCRIPTION OF THE PREFERRED EMBODIMENTS

In accordance with the present invention storage stable organic polyisocyanates characterized by allophanate linkages which are useful for the preparation of polyurethane foam products and the like are prepared by heating a urethane containing organic polyisocyanate such as toluene diisocyanate for a period of about 3 to about 10 hours at temperatures from about 100° C. to about 110° C. in the presence of a metal catalyst. After completion of the desired allophanate reaction, the catalyst is deactivated by the use of a strong inorganic acid, organic acid, organic chloroformate or organic acid chloride.

Organic polyisocyanates which may be employed include aromatic, aliphatic, and cycloaliphatic polyisocyanates and combinations thereof. Representative of these types are the diisocyanates such as m-phenylene diisocyanate, 2,4-toluene diisocyanate, 2,6-toluene diisocyanate, mixtures of 2,4- and 2,6-toluene diisocyanate, hexamethylene diisocyanate, tetramethylene diisocyanate, cyclohexane-1,4-diisocyanate, hexahydrotoluene diisocyanate (and isomers), isophorone diisocyanate, hydrogenated diphenylmethane diisocyanate, naphthalene-1,5-diisocyanate, 1-methoxyphenyl- 2,4-diisocyanate, 4,4'-diphenylmethane diisocyanate, 4,4'-biphenylene diisocyanate, 3,3'-dimethoxy-4,4'-biphenyl diisocyanate, 3,3'-dimethyl-4,4'-biphenyl diisocyanate and 3,3'-dimethyl-diphenylmethane-4,4'-diisocyanate; the triisocyanates such as 4,4', 4"-triphenylmethane triisocyanate, and toluene 2,4,6-triisocyanate; and the tetraisocyanates such as 4,4'-dimethyldiphenylmethane-2,2',5,5'-tetraisocyanate and polymeric polyisocyanates such as polymethylene polyphenylene polyisocyanate. Especially useful due to their availability and properties are toluene diisocyanate, and 4,4'-diphenylmethane diisocyanate.

Crude polyisocyanates may also be used in the compositions of the present invention, such as crude toluene diisocyanate obtained by the phosgenation of a mixture of crude toluene diamines or crude diphenylmethane diisocyanate obtained by the phosgenation of crude diphenylmethane diamine.

The mono- and polyhydric compounds which may be reacted with the polyisocyanate have an equivalent weight of about 30 to about 1000, can contain up to about 8 hydroxyl groups in the molecule, and can also be alkylene oxide adducts thereof.

Monohydric alchols which may be employed include both aliphatic and aromatic alcohols such as methanol, ethanol, propanol, 2-propanol, n-butanol, 2-chloroethanol, pentanol, n-octanol, 2-ethylhexanol, isooctyl alcohol, nonanol, 3,5,5-trimethylhexanol, isodecyl alcohol, benyyl alcohol, cyclohexanol, 2,4,4,4-tetrachloro-1-butanol, 2,3-dichloro-propanol, 2,3-dibromopropanol, 2,2,2-tricholoroethanol, 2,2,2-triboromoethanol, 1,1,1,3,3,3-hexachloro-2-propanol, 1,1-dichloro-2-propanol, 1,3-dibromo-2-propanol, 1,1,1-trichloro-2-propanol, 1,3-dibromo-2-propanol, 1,1,1-trichloro-2-propanol, 1,1,3,3-tetrabromo-2-propanol, the isomeric tribromophenols, the isomeric tetrachlorophenols, pentachlorophenol, 2-methylol-1,4,5,6,7,7-hexachlorobicyclo(2.2.1)-5-heptene and the like and alkylene oxide adducts thereof. The alkylene oxide may be ethylene oxide, propylene oxide, butylene oxide, amylene oxide or mixtures thereof.

Polyhydric alcohols include both aliphatic and aromatic compounds, for example, ethylene glycol, trimethylene glycol, propylene glycol, 1,4-butanediol, 1,3-butanediol, 1,6-hexanediol, 1,7-heptanediol, glycerine, 1,1,1-trimethylolpropane, 1,1,1-trimethylolethane, hexane-1,2,6-triol, a-methyl glucoside, pentaerythritol, sorbitol, diethylene glycol, dipropylene glycol, 2,3-dibromo-2-butenediol-1,4, 2,3-dibromobutanediol-1,4, dibromoneopentyl glycol, 4,4'-isopropylidene diphenol, also know as Bisphenol A, tetrabromobisphenol A, dibromobisphenol A, resorcinol, catechol, hyhroquinone, and alkylene oxide adducts thereof.

The catalysts which may be employed are any which are suitable for the promotion of allophanate linkages. These include metal carboxylates, alcoholates, oxides, phenolates and metal chelates. The preferred catalysts are zinc-, cobalt-, nickel-, ferric-, and aluminum acetylacetonates, dibutyltin dilaurate, dibutyltin oxide, stannous octoate and dibutyltin diacetate.

The catalyst deactivators which may be employed are aliphatic and aromatic acid chlorides such as acetyl chloride, benzoyl chloride, and benzenesulfonyl chloride, oxalyl chloride, adipyl chloride, sebacyl chloride, and carbonyl chloride. Also inorganic acids such as perchloric acid, and strong organic acids such as trifluoromethanesulfonic acid and trifluoroacetic acid may be employed.

Chloroformates may also be employed such as methyl chloroformate, ethyl chloroformate, isopropyl chloroformate, n-butyl chloroformate, sec-butyl chloroformate, and diethylene glycol bis chloroformate.

The isocyanates of the invention are prepared by reacting an organic polyisocyanate as disclosed above with a mono- or polyhydric compound in the presence of a catalyst. The amount of mono- or polyhydric compound employed should not exceed one-half equivalent of mono- or polyhydric compound per equivalent of isocyanate. The reaction may continue for 3 to 10 hours at temperatures of 105° C. ±10° C. Upon completion of the reaction, a catalyst deactivator is added. The reaction mixture is stirred at the reaction temperature for about 15 minutes. The product is cooled and may then be employed for use in polyurethane foam or elastomer formulations.

Polyols which may be employed for the preparation of polyurethane foams and elastomers are well known to those skilled in the art. They are often prepared by the catalytic condensation of an alkylene oxide or mixture of alkylene oxides either simultaneously or sequentially with an organic compound having at least two active hydrogen atoms, such as evidenced by U.S. Pat. Nos. 1,922,459; 3,190,927; and 3,346,557. Representative polyols include polyhydroxyl-containing polyesters, polyoxyalkylene polyether polyols, polyhydroxy-terminated polyurethane polymers, polyhydroxyl-containing phosphorus compounds, and alkylene oxide adducts of polyhydric polythioesters, polyacetals, aliphatic polyols and thiols, ammonia, and amines including aromatic, aliphatic, and heterocyclic amines, as well as mixtures thereof. Alkylene oxide adducts of compounds which contain 2 or more different groups within the above-defined classes may also be used, for example, amino alcohols which contain an amino group and a hydroxyl group. Also, alkylene oxide adducts of compounds which contain one SH group and one OH group as well as those which contain an amino group and an SH group may be used. Generally, equivalent weight of the polyols will vary from 100 to 10,000, preferably from 1000 to 3000.

Any suitable hydroxy-terminated polyester may be used such as are prepared, for example, from polycarboxylic acids and polyhydric alcohols. Any suitable polycarboxylic acid may be used such as oxalic acid, malonic acid, succinic acid, glutaric acid, adipic acid, pimelic acid, suberic acid, azelaic acid, sebacic acid, brassylic acid, thapsic acid, maleic acid, fumaric acid, glutaconic acid, α-hydromuconic acid, β-hydromuconic acid, α-butyl-α-ethyl-glutaric acid, α,β-diethyl-succinic acid, isophthalic acid, terephthalic acid, hemimellitic acid, and 1,4-cyclohexanedicarboxylic acid. Any suitable polyhydric alcohol, including both aliphatic and aromatic, may be used such as ethylene glycol, propylene glycol, trimethylene glycol, 1,2-butanediol, 1,3-butanediol, 1,4-butanediol, 1,2-pentanediol, 1,4-pentanediol, 1,5-pentanediol, 1,6-hexanediol, 1,7-heptanediol, glycerol, 1,1,1-trimethylolpropane, 1,1,1-trimethylolethane, 1,2,6-hexanetriol, α-methyl glucoside, pentaerythritol, and sorbitol. Also included within the term "polyhydric alcohol" are compounds derived from phenol such as 2,2-bis(4-hydroxyphenyl)propane, commonly known as Bisphenol A.

The hydroxyl-containing polyester may also be a polyester amide such as is obtained by including some amine or amino alcohol in the reactants for the preparation of the polyesters. Thus, polyester amides may be obtained by condensing an amino alcohol such as ethanolamine with the polycarboxylic acids set forth above or they may be made using the same components that make up the hydroxyl-containing polyester with only a portion of the components being a diamine such as ethylene diamine.

Any suitable polyoxyalkylene polyether polyol may be used such as the polymerization product of an alkylene oxide or a mixture of alkylene oxides with a polyhydric alcohol. Any suitable polyhydric alcohol may be used such as those disclosed above for use in the preparation of the hydroxy-terminated polyesters. Any suitable alkylene oxide may be used such as ethylene oxide, propylene oxide, butylene oxide, amylene oxide, and mixtures of these oxides. The polyoxyalkylene polyether polyols may be prepared from other starting materials such as tetrahydrofuran and alkylene oxide-tetrahydrofuran mixtures; epihalohydrins such as epichlorohydrin; as well as aralkylene oxides such as styrene oxide. The polyoxyalkylene polyether polyols may have either primary or secondary hydroxyl groups. Included among the polyether polyols are polyoxyethylene glycol, polyoxypropylene glycol, polyoxybutylene glycol, polytetramethylene glycol, block copolymers, for example, combinations of polyoxypropylene and polyoxyethylene glycols, poly-1,2-oxybutylene and polyoxyethylene glycols, poly-1,4-oxybutylene and polyoxyethylene glycols, and random copolymer glycols prepared from blends of two or more alkylene oxides or by the sequential addition of two or more alkylene oxides. The polyoxyalkylene polyether polyols may be prepared by any known process such as, for example, the process disclosed by Wurtz in 1859 and *Encyclopedia of Chemical Technology,* Vol. 7, pp. 257-262, published by Interscience Publishers, Inc. (1951) or in U.S. Pat. No. 1,922,459. Polyethers which are preferred include the alkylene oxide addition products of trimethylolpropane, glycerine, pentaerythritol, sucrose, sorbitol, propylene glycol, and 2,2'-(4,4'-hydroxyphenyl)propane and blends thereof having equivalent weights of from 100 to 5000.

Suitable polyhydric polythioethers which may be condensed with alkylene oxides include the condensation product of thiodiglycol or the reaction product of a dicarboxylic acid such as is disclosed above for the preparation of the hydroxyl-containing polyesters with any other suitable thioether glycol.

Polyhydroxyl-containing phosphorus compounds which may be used include those compounds disclosed in U.S. Pat. No. 3,639,542. Preferred polyhydroxyl-containing phosphorus compounds are prepared from alkylene oxides and acids of phosphorus having an acid equivalency of from about 72 percent to about 95 percent.

Suitable polyacetals which may be condensed with alkylene oxides include the reaction product of formaldehyde or other suitable aldehyde with a dihydric alcohol or an alkylene oxide such as those disclosed above.

Suitable aliphatic thiols which may be condensed with alkylene oxides include alkanethiols containing at least two —SH groups such as 1,2-ethanedithiol, 1,2-propanedithiol, 1,3-propanedithiol, and 1,6-hexanedithiol; alkene thiols such as 2-butene-1,4-dithiol; and alkyne thiols such as 3-hexyne-1,6-dithiol.

Suitable amines which may be condensed with alkylene oxides include aromatic amines such as aniline, o-chloroaniline, p-aminoaniline, 1,5-diaminonaphthalene, methylene dianiline, the condensation products of aniline and formaldehyde, and 2,3- 2,6-, 3,4-, 2,5-, and 2,4-diaminotoluene; aliphatic amines such as methylamine, triisopropanolamine, ethylenediamine, 1,3-diaminopropane, 1,3-diaminobutane, and 1,4-diaminobutane.

Also, polyols containing ester groups can be employed in the subject invention. These polyols are prepared by the reaction of an alkylene oxide with an organic dicarboxylic acid anhydride and a compound containing reactive hydrogen atoms. A more comprehensive discussion of these polyols and their method of preparation can be found in U.S. Pat. Nos. 3,585,185; 3,639,541 and 3,639,542.

Polyols containing graft polymer dispersions may also be employed in the invention. These are prepared by the in situ polymerization, in the polyols listed below, of an ethylenically unsaturated monomer or a mixture of ethylenically unsaturated monomers. Representative ethylenically unsaturated monomers which may be employed in the present invention include butadiene, isoprene, 1,4-pentadiene, 1,6-hexadiene, 1,7-octadiene, styrene, $\alpha$-methylstyrene, 2-methylstyrene, 3-methylstyrene and 4-methylstyrene, 2,4-dimethylstyrene, ethylstyrene, isopropylstyrene, butylstyrene, phenylstyrene, cyclohexylstyrene, benzylstyrene, and the like; substituted styrenes such as cyanostyrene, nitrostyrene, N,N-dimethylaminostyrene, acetoxystyrene, methyl 4-vinylbenzoate, phenoxystyrene, p-vinylphenyl oxide, and the like; the acrylic and substituted acrylic monomers such as acrylonitrile, acrylic acid, methacrylic acid, methyl acrylate, 2-hydroxyethyl acrylate, methyl methacrylate, cyclohexyl methacrylate, benzyl methacrylate, isopropyl methacrylate, octyl methacrylate, methacrylonitrile, ethyl $\alpha$-ethoxyacrylate, methyl $\alpha$-acetaminoacrylate, butyl acrylate, 2-ethylhexyl acrylate, phenyl acrylate, phenyl methacrylate, N,N-dimethylacrylamide, N,N-dibenzylacrylamide, N-butylacrylamide, methacrylyl formamide, and the like; the vinyl esters, vinyl ethers, vinyl ketones, etc., such as vinyl acetate, vinyl butyrate, isopropenyl acetate, vinyl formate, vinyl acrylate, vinyl methacrylate, vinyl methoxyacetate, vinyl benzoate, vinyltoluene, vinylnaphthalene, vinyl methyl ether, vinyl ethyl ether, vinyl propyl ethers, vinyl butyl ethers, vinyl 2-ethylhexyl ether, vinyl phenyl ether, vinyl 2 methoxyethyl ether, methoxybutadiene, vinyl 2-butoxyethyl ether, 3,4-dihydro-1,2-pyran, 2-butoxy-2'-vinyloxy diethyl ether, vinyl methyl ketone, vinyl ethyl ketone, vinyl phosphonates such as vinyl phenyl ketone, vinyl ethyl sulfone, N-methyl-N-vinyl acetamide, N-vinyl-pyrrolidone, vinyl imidazole, divinyl sulfoxide, divinyl sulfone, sodium vinylsulfonate, methyl vinylsulfonate, N-vinyl pyrrole, and the like; dimethyl fumarate, dimethyl maleate, maleic acid, crotonic acid, fumaric acid, itaconic acid, monomethyl itaconate, t-butylaminoethyl methacrylate, dimethylaminoethyl methacrylate, glycidyl acrylate, allyl alcohol, glycol monoesters of itaconic acid, vinyl pyridine, and the like. Any of the known polymerizable monomers can be used and the compounds listed above are illustrative and not restrictive of the monomers suitable for use in this invention. Preferably, the monomer is selected from the group consisting of acrylonitrile, styrene and mixtures thereof.

The amount of ethylenically unsaturated monomer employed in the polymerization reaction is generally from 25 percent to 70 percent, preferably from 30 percent to 45 percent, based on the total weight of the product. The polymerization occurs at a temperature between about 25° C. and 180° C., preferably from 80° C. to 135° C..

The unsaturated polyols or macromers which may be employed in preparing the graft polymer dispersions may be prepared by the reaction of any conventional polyol such as those described above with an organic compound having both ethylenic unsaturation and a hydroxyl, carboxyl, anhydride, isocyanate or epoxy group or they may be prepared by employing an organic compound having both ethylenic unsaturation and a hydroxyl, carboxyl, anhydride, or epoxy group as a reactant in the preparation of the conventional polyol. Representative of such organic compounds include unsaturated mono- and polycarboxylic acids and anhydrides such as maleic acid and anhydride, fumaric acid, crotonic acid and anhydride, propenyl succinic anhydride, acrylic acid, acryoyl chloride, hydroxy ethyl acrylate or methacrylate and halogenated maleic acids and anhydrides, unsaturated polyhydric alcohols such as 2-butene-1,4-diol, glycerol allyl ether, trimethylolpropane allyl ether, pentaerythritol allyl ether, pentaerythritol vinyl ether, pentaerythritol diallyl ether, and 1-butene-3,4-diol, unsaturated epoxides such as 1-vinylcyclohexene-3,4-epoxide, butadiene monoxide, vinyl glycidyl ether(1-vinyloxy-2,3-epoxy propane), glycidyl methacrylate and 3-allyloxypropylene oxide (allyl glycidyl ether). If a polycarboxylic acid or anhydride is employed to incorporate unsaturation into the polyols, it is preferable to react the unsaturated polyol with an alkylene oxide, preferably ethylene or propylene oxide, to replace the carboxyl groups with hydroxyl groups prior to employment in the present invention. The amount of alkylene oxide employed is such as to reduce the acid number of the unsaturated polyol to about 5 or less.

Illustrative polymerization initiators which may be employed are the well-known free radical types of vinyl polymerization initiators such as the peroxides, persulfates, perborates, percarbonates, azo compounds, etc. These include hydrogen peroxide, dibenzoyl peroxide, acetyl peroxide, benzoyl hydroperoxide, t-butyl hydroperoxide, di-t-butyl peroxide, lauroyl peroxide, butyryl peroxide, diisopropylbenzene hydroperoxide, cumene hydroperoxide, paramenthane hydroperoxide, diacetyl peroxide, di-$\alpha$-cumyl peroxide, dipropyl peroxide, diisopropyl peroxide, isopropyl-t-butyl peroxide, butyl-t-butyl peroxide, difuroyl peroxide, bis(triphenylmethyl) peroxide, bis(p-methoxybenzoyl) peroxide, p-monomethoxybenzoyl peroxide, rubene peroxide, ascaridol, t-butyl peroxybenzoate, diethyl peroxyterephthalate, propyl hydroperoxide, isopropyl hydroperoxide, n-butyl hydroperoxide, t-butyl hydroperoxide, cyclohexyl hydroperoxide, trans-decalin hydroperoxide, $\alpha$-methylbenzyl hydroperoxide, $\alpha$-methyl-$\alpha$-ethyl benzyl hydroperoxide, tetralin hydroperoxide, triphenylmethyl hydroperoxide, diphenylmethyl hydroperoxide, $\alpha,\alpha'$-azobis-(2-methyl heptonitrile), 1,1'-azo-bis(cyclohexane carbonitrile), 4,4'-azobis(4-cyanopentanoic acid), 2,2'-azobis(isobutyronitrile), 1-t-butylazo-1-cyanocyclohexane, persuccinic acid, diisopropyl peroxy dicarbonate, 2,2'-azobis(2,4-dimethylvaleronitrile), 2-t-butylazo-2-cyano-4-methoxy-4-methylpentane,2,2'-azobis-2-methylbutanenitrile, 2-t-butylazo-2-cyanobutane, 1-t-amylazo-1-cyanocyclohexane, 2,2'-azobis(2,4-dimethyl-4-methoxyvaleronitrile), 2,2'-azobis-2-methylbutyronitrile, 2-t-butylazo-2-cyano-4-methylpentane, 2-t-butylazo-2-isobutyronitrile, to butylperoxyisopropyl carbonate and the like; a mixture of initiators may also be used. The preferred initiators are 2,2'-azobis(2-methylbutyronitrile), 2,2'-azobis(isobutyronitrile), 2,2'-azobis(2,4-dimethylvaleronitrile), 2-t-butylazo-2-cyano-4-methoxy-4-methylpentane, 2-t-butylazo-2-cyano-4-methylpentane, 2-t-butylazo-2-cyano-butane and lauroyl peroxide. Generally, from about 0.1 percent to about 10 percent, preferably from about 1 percent to about 4 percent, by weight of initator based on the weight of the monomer will be employed in the process of the invention.

The polyurethane foams employed in the present invention are generally prepared by the reaction of a polyether polyol or a graft polymer dispersion in a polyol as disclosed above with the allophanate containing polyisocyanate in the presence of a blowing agent and optionally in the presence of additional polyhydroxyl-containing components, chain-extending agents, catalysts, surface-active agents, stabilizers, dyes, fillers and pigments. Suitable processes for the preparation of cellular polyurethane products are disclosed in U.S. Pat. No. Re. 24,514 together with suitable machinery to be used in conjunction therewith. When water is added as the blowing agent, corresponding quantities of excess isocyanate to react with the water and produce carbon dioxide may be used. It is possible to proceed with the preparation of the polyurethane products by a prepolymer technique wherein an excess of the allophanate containing polyisocyanate is reacted in a first step with a polyol to prepare a prepolymer having free isocyanate groups which is then reacted in a second step with water and/or additional polyol to prepare a foam. Alternatively, the components may be reacted in a single working step commonly known as the "one-shot" technique of preparing polyurethanes. Furthermore, instead of water, low boiling hydrocarbons such as pentane, hexane, heptane, pentene, and heptene; azo compounds such as azohexahydrobenzodinitrile; halogenated hydrocarbons such as dichlorodifluoromethane, trichlorofluoromethane, dichlorodifluoroethane, vinylidene chloride, and methylene chloride may be used as blowing agents.

Chain-extending agents which may be employed in the preparation of the polyurethane foams include those compounds having at least two functional groups bearing active hydrogen atoms such as water, hydrazine, primary and secondary diamines, amino alcohols, amino acids, hydroxy acids, glycols, or mixtures thereof. A preferred group of chain-extending agents includes water, ethylene glycol, 1,4-butanediol and primary and secondary diamines which react more readily with the prepolymer than does water such as phenylene diamine, 1,4-cyclohexane-bis-(methylamine), ethylenediamine, diethylenetriamine, N-(2-hydroxypropyl)ethylenediamine, N,N'-di(2-hydroxypropyl)ethylenediamine, piperazine, and 2-methylpiperazine.

Any suitable catalyst may be used including tertiary amines such as, for example, triethylenediamine, N-methylmorpholine, N-ethylmorpholine, diethylethanolamine, N-cocomorpholine, 1-methyl-4-dimethylaminoethylpiperazine, 3-methoxypropyldimethylamine, N,N,N'-trimethylisopropyl propylenediamine, 3-diethylaminopropyldiethylamine, dimethylbenzylamine, and the like. Other suitable catalysts are, for example, stannous chloride, dibutyltin di-2-ethyl hexanoate, stannous oxide, as well as other organometallic compounds such as are disclosed in U.S. Pat. No. 2,846,408.

A surface-active agent is generally necessary for production of high grade polyurethane foam according to the present invention, since in the absence of same, the foams collapse or contain very large uneven cells. Numerous surface-active agents have been found satisfactory. Nonionic surface active agents are preferred. Of these, the nonionic surface-active agents such as the well-known silicones have been found particularly desirable. Other surface-active agents which are operative, although not preferred, include polyethylene glycol ethers of long chain alcohols, tertiary amine or alkanolamine salts of long chain alkyl acid sulfate esters, alkyl sulfonic esters, and alkyl arylsulfonic acids.

Among the flame retardants which may be employed are: pentabromodiphenyl oxide, dibromopropanol, tris($\beta$-chloropropyl)phosphate, 2,2-bis(bromoethyl) 1,3-propanediol, tetrakis(2-chloroethyl)ethylene diphosphate, tris(2,3-dibromopropyl)phosphate, tris($\beta$-chloroethyl)phoshate, tris(1,2-dichloropropyl)phosphate, bis-(2-chloroethyl) 2-chloroethylphosphonate, molybdenum trioxide, ammonium molybdate, ammonium phosphate, pentabromodiphenyloxide, tricresyl phosphate, hexabromocyclododecane, melamine, and dibromoethyl- dibromocyclohexane. The concentrations of flame retardant compounds which may be employed range from 5 to 25 parts per 100 parts of polyol mixture.

The following examples illustrate the nature of the invention. All parts are by weight unless otherwise stated. The abbreviations employed are as follows:

TDI is 2,4 -,2,6-toluene diisocyanate.
EG is ethylene glycol
Catalyst A is zinc acetylacetonate.
Catalyst B is nickel acetylacetonate.
Catalyst C is aluminium acetylacetonate.
Catalyst D is ferric acetylacetonate.
Catalyst E is cobalt acetylacetonate.
Catalyst F is dibutyltin dilaurate
Compound A is o,p-methyl-p-toluenesulfonate
Polyol A is a propylene oxide, ethylene oxide adduct of trimethylolpropane containing 15 percent ethylene oxide and having a hydroxyl number of about 25.
Polyol B is a propylene oxide ethylene oxide adduct of glycerine containing 21 percent ethylene oxide and having a hydroxyl number of about 27.5
Polyol C is a propylene oxide ethylene oxide adduct of glycerine containing 17 percent ethylene oxide, 20% of 1:1 acrylonitrile:styrene and having a hydroxyl number of about 29.
Polyol D is a propylene oxide ethylene oxide adduct of glycerine containg 68 percent ethylene oxide and having a hydroxyl number of about 46.
Polyol E is a propylene oxide, ethylene oxide adduct of ethylenediamine containing 10 percent ethylene oxide and having a hydroxyl number of about 453.
Polycat 16 is a catalyst sold by Air Products Corp.
NIAX A-1 is a catalyst sold by Union Carbide Corp.
Dabco 33LV is a catalyst sold by Air Products Corp.
Dow 5043 is a silicone surfactant sold by Dow Corning Corp.

EXAMPLES 1–10

The indicated amount of TDI, was placed into a clean, dry, and nitrogen-purged reactor. Agitation in the reactor was started and continued throughout the reaction. The indicated catalyst was then added to the reaction mixture at a constant rate over a period of 30 minutes. An exothermic reaction ensued. The contents were then heated to 100° C. and maintained at that temperature for the indicated amount of time. Benzoyl chloride was then added and blended at 100° C. for 15 minutes. The heat was turned off and the appropriate amount of the second charge of TDI was added. The starting materials employed, the reaction conditions used, and products prepared are summarized in Table I. Analyses of these products after six months' storage under ambient conditions indicated the excellent long-term storage stability of these products. There was no loss in NCO content and no increase in viscosity. Examples 9 and 10 represent comparative examples based on the prior art teachings of U.S. Pat. No. 3,769,318.

TABLE I

| Example | 1 | 2 | 3 | 4 | 5 | 6 | 7 | 8 | 9 | 10 |
|---|---|---|---|---|---|---|---|---|---|---|
| TDI | 631.6 | 3158 | 3185 | 3158 | 789.5 | 789.5 | 789.5 | 290.5 | 1914 | 3158 |
| EG | 20.5 | 102.3 | 102.3 | 102.3 | 25.6 | 25.6 | 25.6 | 9.5 | 62 | 102.3 |
| Catalyst A | 0.19 | 0.95 | 0.54 | | | | | | 0.5 | 0.219 |
| Catalyst B | | | | 0.54 | | | | | | 0.352 |
| Catalyst C | | | | | | 0.139 | | | | |
| Catalyst D | | | | | 0.136 | | | | | |
| Catalyst E | | | | | | | 0.139 | | | |
| Catalyst F | | | | | | | | 0.12 | | |
| Compound A | | | | | | | | | 2.0 | 1.69 |
| Benzoyl Chloride | 0.4 | 2.0 | 1.0 | 1.0 | — | 0.13 | 0.13 | 0.12 | — | — |
| Reaction Time, hrs. | 3 | 3 | 5 | 5.5 | 5 | 5 | 5 | 5 | 7 | 11 |
| Reaction Temp., °C. | 100 ± 2 | | | | | | | 110 ± 2 | 100 ± 2 | 100 ± 2 |
| % NCO | 37.9 | 38.9 | 39.1 | 39.1 | 39.8 | 41.8 | 39.5 | 40.0 | 38.8 | 38.9 |
| TDI added | 223 | 681.1 | 580 | 607 | 145.2* | — | — | — | — | 680 |
| % Final NCO | 40.7 | 40.4 | 40.5 | 40.6 | — | — | — | — | — | 40.6 |

*contained 0.13 g benzoyl chloride.

EXAMPLE 11

A high resilience flexible polyurethane foam was prepared using the isocyanate of Example 1. The formulation employed and the resulting foam properties are shown in Table II. This foam with excellent properties demonstrates the utility of the allophanate isocyanate compositions of the invention.

TABLE II

| Example | 11 |
|---|---|
| Formulation | |
| Polyol A | 3086 |
| Polyol B | 25.54 |
| Polyol C | 35.00 |
| Polyol D | 1.00 |
| Polyol E | 3.00 |
| Polycat 16 | 0.60 |
| A-1 | 0.20 |
| Dabco 33LV | 0.15 |
| Dow 5043 | 1.20 |
| H$_2$O | 2.45 |
| Isocyanate of Example 1 | 36 |
| Physical Properties | |
| Density, kg,/m$^3$ | 48.05 |
| Tear strength, n/m | 218.9 |
| Tensile strength, kPa | 144.8 |
| Elongation, % | 125 |
| ILD | |
| 25%, kg | 18.1 |
| 65%, kg | 52.2 |
| 25% return, kg | 13.6 |
| Recovery, % | 75 |
| Sag factor | 2.87 |
| Compression Set, 50% | 10.9 |

The embodiments of the invention in which an exclusive property or privilege is claimed are defined as follows:

1. A process for the preparation of liquid storage stable allophanate polyisocyanate comprising reacting an excess of an organic polyisocyanate with a mono or polyhydric compound in the presence of an organo metal catalyst wherein said catalyst is deactivated by a compound selected from the group consisting of
    (a) organic acids selected from the group consisting of trifluoromethane sulfonic acid and trifluoroacetic acid,
    (b) organic acid chlorides selected from the group consisting of acetyl chloride, benzoyl chloride, benzenesulfonyl chloride, oxalyl chloride, adipyl chloride, sebacyl chloride and carbonyl chloride, and
    (c) organic chlorofomates selected from the group consisting of methyl chloroformate, ethyl chloroformate, isopropyl chloroformate, n-butyl chloroformate, sec-butyl chloroformate and diethylene glycol bis-chloroformate.

2. The process of claim 1 wherein the organic polyisocyanate is toluene diisocyanate.

3. The process of claim 1 wherein the monohydric compound is selected from the group consisting of methanol, ethanol, propanol, butanol, pentanol and alkylene adducts thereof.

4. The process of claim 1 wherein the polyhydric compound is selected from the group consisting of ethylene glycol, propylene glycol, glycerine, 1,4-butanediol, 1,3-butanediol, diethylene glycol and dipropylene glycol.

5. The process of claim 1 wherein the catalyst is selected from the group consisting of zinc acetylacetonate, cobalt acetylacetonate, nickel acetylacetonate, ferric acetylacetonate and aluminum acetylacetonate.

6. The process of claim 1 wherein the catalyst is deactivated by benzoyl chloride.

* * * * *